United States Patent
Malhotra et al.

(10) Patent No.: US 8,522,775 B2
(45) Date of Patent: *Sep. 3, 2013

(54) DRY POWDER INHALER

(75) Inventors: Geena Malhotra, Mumbai (IN); Amar Lulla, Mumbai (IN)

(73) Assignee: CIPLA Limited, Mumbai (IN)

( * ) Notice: Subject to any disclaimer, the term of this patent is extended or adjusted under 35 U.S.C. 154(b) by 831 days.

This patent is subject to a terminal disclaimer.

(21) Appl. No.: 12/305,199

(22) PCT Filed: Jun. 15, 2007

(86) PCT No.: PCT/GB2007/002257
§ 371 (c)(1),
(2), (4) Date: Jun. 9, 2009

(87) PCT Pub. No.: WO2007/144659
PCT Pub. Date: Dec. 21, 2007

(65) Prior Publication Data
US 2009/0320838 A1     Dec. 31, 2009

(30) Foreign Application Priority Data
Jun. 16, 2006 (IN) .......................... 957/MUM/2006

(51) Int. Cl.
*A61M 16/00* (2006.01)
(52) U.S. Cl.
USPC ............. 128/203.15; 128/203.21; 128/205.21
(58) Field of Classification Search
USPC ............. 128/200.23, 203.15, 203.21, 205.21
See application file for complete search history.

(56) References Cited

U.S. PATENT DOCUMENTS

| | | | | | |
|---|---|---|---|---|---|
| 3,807,400 | A | * | 4/1974 | Cocozza ................... | 128/203.15 |
| 3,906,950 | A | * | 9/1975 | Cocozza ................... | 128/203.15 |
| 4,069,819 | A | * | 1/1978 | Valentini et al. ......... | 128/203.15 |
| 5,896,855 | A | * | 4/1999 | Hobbs et al. ............. | 128/203.15 |
| 6,705,313 | B2 | * | 3/2004 | Niccolai ................... | 128/203.21 |
| 7,708,014 | B2 | * | 5/2010 | Yamashita et al. ........ | 128/203.15 |
| 8,006,695 | B2 | * | 8/2011 | Lulla et al. ............... | 128/203.21 |
| 2005/0048003 | A1 | | 3/2005 | Ohki et al. | |

FOREIGN PATENT DOCUMENTS

| | | |
|---|---|---|
| GB | 2407042 A | 4/2005 |
| WO | 2006051300 A | 5/2006 |

OTHER PUBLICATIONS

International Search Report. PCT/GB2007/002257. Mailed Oct. 4, 2007.

* cited by examiner

*Primary Examiner* — Lynne Anderson
(74) *Attorney, Agent, or Firm* — Conley Rose, P.C.; Rodney B. Carroll

(57) ABSTRACT

An inhaler (1) device for inhalation of a medicament from a pierceable capsule (10) comprises a housing (2) for receiving a medicament, capsule, closure means (3) for closing the housing, said closure means being moveable relative to the housing; piercing means (7) suitable for piercing a medicament capsule; wherein movement of the closure means relative to the housing causes movement of the piercing means, and wherein the device comprises an air inlet (71) and an air outlet (72) defining an inhalation passage therebetween, the passage comprising one or more vents (70).

48 Claims, 6 Drawing Sheets

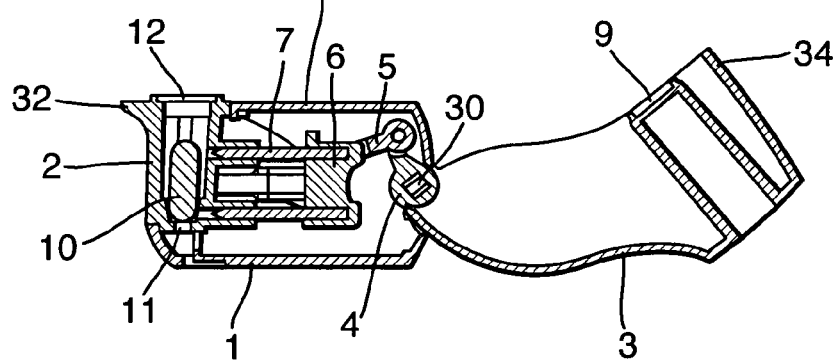
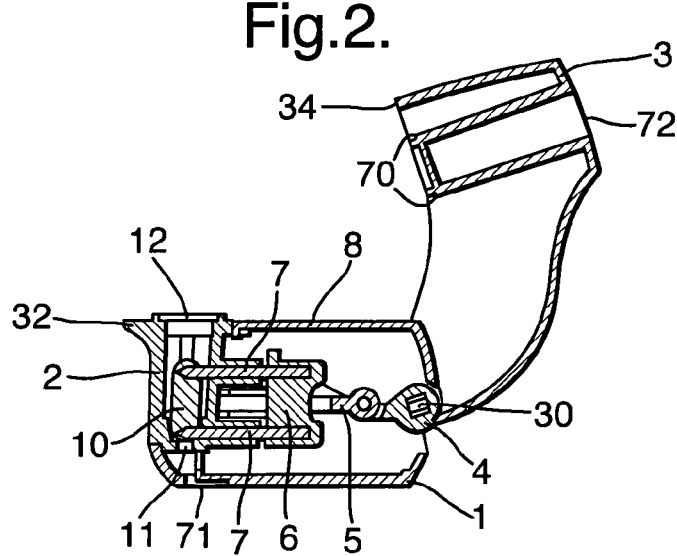
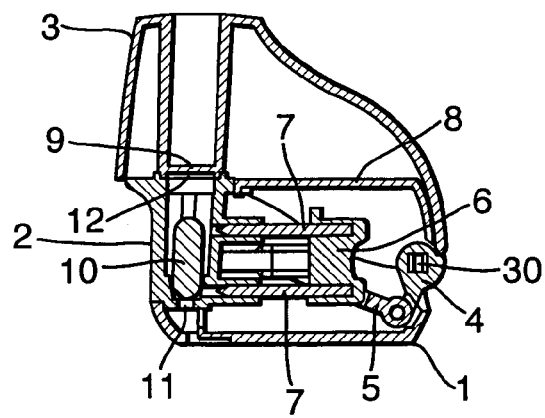

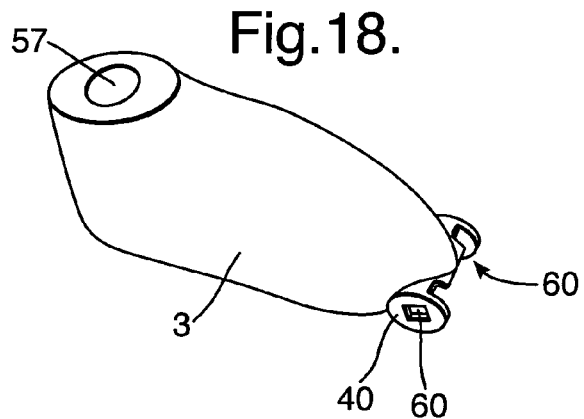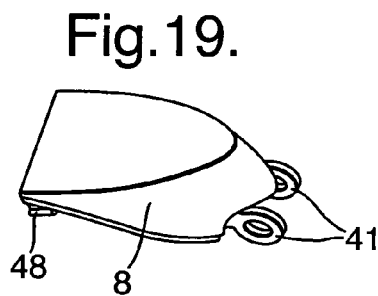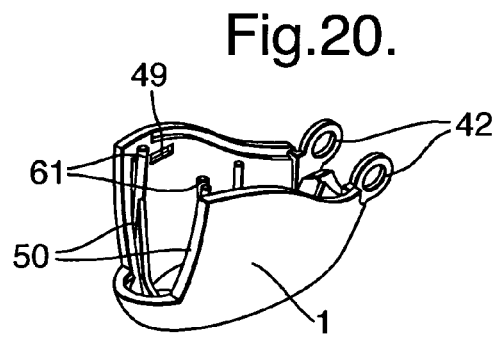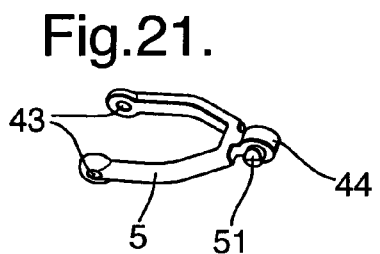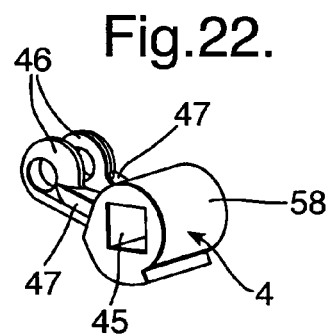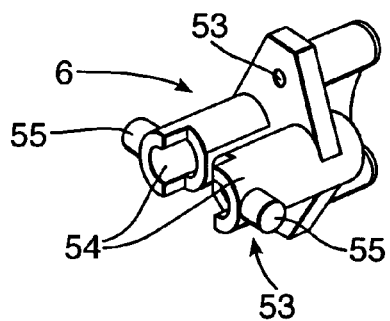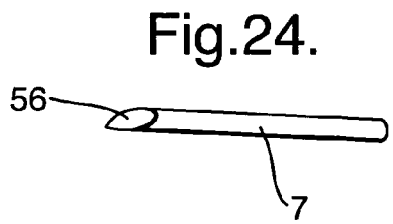

DRY POWDER INHALER

CROSS-REFERENCE TO RELATED APPLICATIONS

This application is a national stage application under 35 USC §371(c) of PCT Application No. PCT/GB2007/002257, entitled "IMPROVED DRY POWDER INHALER," filed Jun. 15, 2007, which claims priority from Indian Patent Application No. 957/MUM/2006, filed Jun. 16, 2006 all of which are hereby incorporated by reference herein.

The present invention relates to an inhalation device for inhalation of medicaments, and to a holder for such medicaments.

Dry powder inhalation (DPI) devices are generally used for inhalation of powdered medicament from capsules. The DPI devices may either single dose or multidose. In the single dose or multiple unit dose DPI formulations, the drug is pre-packaged in capsules or blisters. The reservoir DPI formulations involve a device containing at least a reservoir and a metering chamber to administer an accurate dose of the drug.

Medicament holders, particularly for inhalation devices known in the art are used for receiving and holding a medicament in granular form or powder form, or volatile form or in a capsule containing powdered or volatile medicament. The configuration of the holder is such that the medicament or the capsule located inside the chamber is rotated or moved up and down by air flowing through the chamber in order to disperse the powdered drug medicament into air being sucked.

The medicament holders, for example capsule chambers, known in the art are generally tubular or cylindrical in shape with an air inlet and air outlet arranged coaxially at the bottom and top ends respectively. The air inlet is generally smaller and outlet opening generally larger than the diameter of the capsule. A mouthpiece is arranged axially to the air outlet. Generally, a piercing mechanism is provided to pierce the capsule to enable the medicament present in the capsule to be inhaled. During inhalation, air passes from the air inlet and causes movement of the capsule, and due to this, the medicament present in the capsule is carried by the air to the air outlet opening and mouthpiece and reaches the patient's lungs.

Single dose DPI devices working with capsules, usually possess a system to pierce the capsule. After piercing, the patient inhales the powder contained in the capsule through the device without swallowing the capsule. The capsule remains in the device which is discarded from the device prior to the next use of the device.

WO 91/06333 describes a device for dispensing single doses of a powdered medicament from a container having a plurality of apertures, each of which holds a respective one of said doses, and is sealed by two opposed seals. The device comprises a housing for holding the container, the housing having an outlet and an airway, which communicates with the outlet and being configured to allow the container to move relative thereto to bring each aperture in succession into registry with the airway. The device includes a piercing member movable from a retracted position in which it is positioned clear from the container into an extended position in which it extends into the aperture, said movement causing rupture of the seals, while expelling substantially no medicament from the aperture.

U.S. Pat. No. 5,685,294 discloses an inhaler for inhalation of powdered medicament, more particularly a microionised drug preparation, from capsules, the housing of the inhaler comprising tubular chambers for receiving and holding medicament-containing capsules in a revolver magazine with an air inlet at the bottom and an air outlet at the opposite end of the chamber opening into a mouth piece, a cutting device with two blades which are movable into the interior of the chamber in order to open the capsules near the top and bottom ends thereof.

U.S. Pat. No. 3,807,400 discloses an inhaler comprising an upper member comprising a whirling chamber; a lower member comprising a capsule-receiving chamber and a series of cams and recesses on the inner wall of the lower member; and piercing members resiliently biased away from a capsule received in the capsule-receiving chamber by the action of a spring. In use, rotation of upper and lower members relative to each other causes reciprocations of the piercing members against the cams and recesses provided on the inner wall of the lower member, so as to effect a number of diametrically opposed piercing operations on the capsule.

U.S. Pat. No. 3,795,244 discloses an inhaler comprising a housing; a rotary member located within the housing and having at one end engagement means adapted to receive a medicament-containing capsule; and a piercing assembly comprising opposed arms with piercing pins mounted thereon and a tubular member slidable relative to the housing and having cam projections from the inner wall. In use, and prior to inhalation, the user inserts a capsule into the engagement means and is then required to manually slide the tubular member towards the mouthpiece, so that the cams provided on the inner wall of the tubular member push opposed piercing arms towards the capsule, resulting in perforation of the capsule at its free end. The user is then required to manually return the tubular member to its original position, allowing the piercing arms to return to the non-piercing position.

U.S. Pat. No. 4,069,819 discloses a dry powder inhaler device comprising a nebulising chamber adapted to receive a medicament-containing capsule. A capsule received in the chamber is freely moveable within it. In use, air flow through the nebulising chamber and around the capsule contained therein causes the entire capsule to move within the nebulisation chamber.

U.S. Pat. No. 3,635,219 discloses a dry powder inhaler device comprising a propeller-like member rotatably mounted in a housing and having mounting means adapted to receive a medicament-containing capsule. In use, flow of inhaled air through the device causes rotation and vibration of the propeller-like member and a capsule mounted thereon, so dispensing medicament into the air stream. The device further comprises spring-loaded piercing members mounted in the housing so as to be normally urged into an inoperative position but which may be manually pushed inwards to perforate a medicament containing-capsule received in the device by the action of pushbuttons or sliding cams.

U.S. Pat. No. 3,906,950 describes a dry powder inhalation device comprising a swirl compartment and, separately, a capsule-receiving cavity comprising two components, said cavity slidably attached to a pair of relatively moveable elements which hold piercing needles and which telescopically slide inside capsule holder components against the action of a pair of return springs.

U.S. Pat. No. 5,947,118 relates to a capsule holder for receiving two part capsules, which holder comprises a recess adapted to receive a capsule, wherein the sidewalls of the recess have three or more ribs arranged parallel to the central axis of the recess between which capsules can be clamped by both upper and lower parts with some deformation of the capsule walls. The relative dimensions of the cylinder defined by the ribs and the capsule is such that in use, a capsule received by the ribs is clamped and held firmly in place within the holder.

U.S. Pat. No. 4,889,114 discloses a dry powder inhaler device comprising a capsule-receiving chamber comprising an air inlet and an air outlet located at opposed ends of the chamber. In use, air flow through the chamber on inhalation causes movement of a capsule received therein, between the air inlet end and the air outlet end of the capsule-receiving chamber. The capsule is freely moveable within the confines of the chamber.

All the known inhalation devices require the user of the device to open the device, insert a medicament-containing capsule, close the device, and pierce the capsule manually by a pushing or rotating action prior to inhalation of the medicament. The user has to perform numerous actions before actual inhalation of the medicament.

We have found that the known medicament holders also have the disadvantage of requiring the user of the inhaler to inhale very deeply in order to try to inhale the full dose of the medicament.

One improved inhaler is described in our application WO 2006/051300. We have now made further improvements over the known devices and holders.

In its broadest aspect, the present invention provides an inhaler device for inhalation of a medicament from a pierceable capsule, which inhaler comprises a housing for receiving a medicament capsule; closure means for closing the housing, said closure means being moveable relative to the housing; piercing means suitable for piercing a medicament capsule; wherein movement of the closure means relative to the housing causes movement of the piercing means; and wherein the device comprises an air inlet and an air outlet defining an inhalation passage therebetween, the passage comprising one or more vents.

In another aspect of the present invention, there is provided an inhaler device for inhalation of a medicament from a pierceable capsule, which inhaler comprises a housing for receiving a medicament capsule; closure means for closing the housing, said closure means being moveable relative to the housing; piercing means suitable for piercing a medicament capsule; and linking means connected to both the closure means and the piercing means, wherein movement of the closure means causes movement of the linking means so as to move the piercing means; and wherein the device comprises an air inlet and an air outlet defining an inhalation passage therebetween, the passage comprising one or more vents.

Thus, in use, piercing or perforation of a capsule received in the housing occurs as a consequence of merely closing the housing subsequent to having placed a medicament-containing capsule therein. The user is not required to perform any additional actions prior to inhalation of medicament from the inhaler device, other than inserting a capsule and closing the device.

Preferably, the medicament contained within the capsule is a dry powder medicament. The term capsule is intended to be understood broadly and includes any suitable receptacle for medicament. The capsule may be formed from any suitable material, including gelatin, HPMC, or plastic.

The device may be made from any suitable material. Preferably the device is made of plastic, for example ABS (acrylonitrile butadiene styrene), PC (polycarbonate), PA (polyacetal) or PS (polystyrene), or mixtures thereof, or of an antistatic material such as delrin.

We have found that the inclusion of one more vents enables the patient to inhale more easily, because of a reduced resistance to air flow. In other words, the perceived resistance to inhalation experienced by the user is lower. The resistance to airflow through a dry powder inhaler can be quantified by applying a standard pressure drop across the device and measuring the flow rate through the device. We have compared the resistance to airflow of the illustrated embodiment of the present device with the inhaler described in our WO 2006/051300 using standard apparatus for measuring flow rates from dry powder inhalers, as further described in the US Pharmacopeia-NF (USP30-NF 25). A standard pressure drop of 4 Kpa was applied across each device and the flow rate measured. The following results were obtained: present device: 50 ml/minute; device of WO 2006/051300: 30 ml/minute. The results indicate that the present inhaler is a much lower resistance device, meaning much less effort is required by the user to achieve the same dose of medicament.

It will be appreciated that the inhaler device will comprise at least one main primary air inlet through which air is initially drawn from the atmosphere into the device. Likewise, the device will also comprise a final air outlet through which inhaled air exits the device and enters the patient's mouth. Between this initial air inlet and final air outlet, the device will define a passageway through the body of the device through which air flows. The passageway is referred to herein as the inhalation passage. The invention provides one or more vents, which it will be understood are essentially auxiliary air inlets, positioned at one or more points along the inhalation passage. The vents are essentially small openings in the wall of the inhalation passage, which serve to connect air in the inhalation passage with air external to the passage.

Preferably, two vents, which suitably oppose each other, are employed, although one vent, or more than two vents may be employed if desired. The vents can be of any suitable shape and size, although they are preferably crescent-shaped.

It is preferred to position these vents upstream of the medicament capsule, relative to the flow of air through the inhalation passage.

The closure means can be moveable relative to the housing in any suitable way. The closure means is typically connected to the housing, although they may, if desired be separate parts. Suitably, the closure means is adapted to, or comprises suitable means for, producing movement of the piercing means so as to cause piercing of a capsule. Preferably, the closure means is rotatable relative to the housing. For example, the closure means may be pivotally connected to the housing. Preferably, movement of the closure means causes movement or rotation of a linking means. In one embodiment, rotation of the closure means drives linear displacement of the piercing means. However, the movement of the piercing means is not limited and the piercing means may move in any way, so long as the object of piercing a capsule is achieved. For example, we envisage rotary motion of the piercing means as a possibility.

The movement of the closure means preferably moves the piercing means so as to pierce a capsule positioned within the inhaler housing. Suitably, movement of the closure means from a fully open or fully closed position drives movement of the piercing means from a fully retracted position. The piercing means preferably moves from a fully retracted position to a fully extended piercing position and back to a fully retracted position in response to movement of said closure means between the fully open and fully closed piercing positions.

The housing preferably comprises means to hold a medicament capsule, said holding means preferably comprising a chamber having one or more air inlets and air outlet(s). The air inlet of the chamber may constitute the air inlet of the device, or the air inlet of the device may be provided separately on the device, for example elsewhere on the housing. The or each air inlet and outlet are preferably provided at opposing ends of the chamber. In a preferred embodiment, the or each air inlet is positioned in, or near to, the base of the medicament holder. They may, for example, be provided on the walls of the chamber, for example on the lower walls. The flow of air via the or each inlet may be at a tangent to, or at an angle offset from, the longitudinal axis of the chamber. In one embodiment, a single air inlet may be used. Alternatively, two or more inlets may be used. For example, two air inlets may be provided at or near the bottom of the holder. Preferably, they are provided in the lower vertical walls of the chamber. For example, two inlets may be provided substantially opposite to one another in the lower walls. These inlets may, if desired, be offset from one another; for example in a tangential arrangement.

The interior of the chamber may be of any suitable shape and dimension. It may, for example, define a single cavity of uniform dimensions Alternatively, the interior of the chamber may comprise one or more steps such that the internal cavity is non-uniform. One additional step in the interior of the chamber is preferred. The or each step is preferably substantially perpendicular with the respect to the longitudinal axis of the chamber, although any suitable angle may be employed.

The closure means preferably comprises a mouthpiece. That is to say, the closure means is preferably such that it includes means by or via which medicament may be inhaled from the device by the user. In what follows, the invention is described with reference to a device wherein the closure means comprises a mouthpiece, it being understood that the invention includes embodiments wherein the closure means may not necessarily comprise or include a mouthpiece. For example, the closure means and mouthpiece could be separate. Thus, in what follows, it is to be understood that references to a mouthpiece may be substituted with references to closure means. The inhaler mouthpiece is preferably pivotably attached to the housing.

The air outlet of the medicament chamber is suitably positioned so as to connect or coincide with the mouthpiece in its fully closed position. For example, the mouthpiece may suitably comprise means to receive air from an outlet of the medicament chamber, such that when the mouthpiece is closed the means for receiving air is connected with, or cooperates with, the outlet. Any suitable means may be used, for example a tube, which may for example be cylindrical. Conical means may be used. The means may be formed as an integral part of the mouthpiece or may be a separate part. Suitably, the means (e.g. a tube which may be cylindrical or oval shaped in cross section) comprises one end which connects with the outlet of the medicament chamber, and another end which comprises an outlet for the medicament, from which outlet medicament is inhaled by the user. It is preferred that the end which connects with the outlet of the medicament chamber comprises the vents, preferably two opposing crescent-shaped vents positioned at either side. The arrangement is preferably such that the vents are in close proximity to the outlet of the medicament chamber. The outlet of the said means may constitute the final air outlet of the inhaler device. Preferably, the positioning, in particular the angle, of the vents is such that in use the direction of airflow through the vents is in the same general direction as the direction of the main inhalation airflow through the inhalation passage. It will be understood the vents are typically formed as a hole or opening through the thickness of one or more walls of the inhalation passage. Where the wall thickness is such that an axis through the vent can be defined, the axis of the vent is preferably at an angle of less than 90 degrees, more preferably 45 degrees or less, relative to the direction of the main inhalation airflow through the inhalation passage. That is to say, the flow of air through the vents into the inhalation passage is preferably not perpendicular to, or against, the main inhalation flow, but flows in the same general direction.

The portion or means of the mouthpiece adapted to receive air (for example the tube described above) from the medicament chamber is preferably of an optimised length. Preferably, the length is between about 25 and 35 mm. We have found a length of 31.6 mm+/−10% to give very good performance. Suitably, two crescent-shaped vents may be positioned one at either side of the tube at a distance of about from 4 to 6 mm, ideally about 5 mm, from the end of the tube which cooperates with the outlet of the medicament chamber.

The mouthpiece is preferably provided with a mesh which is positioned in proximity to the chamber outlet when the mouthpiece is in a fully closed position. Preferably, the mesh is provided on a means for receiving air from the outlet of the chamber. Preferably, the mesh is on, or near to, the end of the said means (for example, a tube), such that the mesh is brought into proximity with the outlet of the medicament chamber when the mouthpiece is in the closed position. The mesh may be provided as a separate part or as an integral part of the device. A mesh may if desired also, or alternately, be provided on or close to the outlet of the medicament chamber. Again, the mesh may be an integral or a separate part. The primary function of the mesh is to prevent the capsule or fragments thereof from being inhaled by the user. The vents are preferably positioned in proximity to the mesh.

The device preferably further comprises locking means. The locking means suitably locks the closure means, for example the mouthpiece, in a predetermined position relative to the housing. Preferably, the locking means is operable to retain said closure means in the fully closed position. The locking means may provide a rigid pivot for the opening and closing of the device. Alternatively, the locking means may comprise a lip or suitable projection on a portion of the capsule holder adapted to be received by a portion of the closure means, for example to provide a snap-fit. Preferably, the arrangement is such as to secure or lock the mouthpiece in the closed position.

The piercing means may be any suitable means but preferably comprises one or more piercing pins and/or one or more blades, although piercing pins are most preferred. The piercing means (suitably pins) may be of any suitable material, and are preferably metallic. For example, stainless steel may be used.

The device preferably further comprises guide means to guide the movement of the piercing means. For example, the guide means may comprise one or more tubes extending from an external part of the medicament chamber. One or more suitable holes may be provided in the chamber, the arrangement being such that the guiding means serve to guide the piercing means through the said holes so as pierce a capsule.

The mouthpiece (3) preferably coincides with the outlet (12) of the capsule holder (2) so as to receive the medicament during inhalation. Preferably, a link actuator (4) adapts the link (5) to the mouthpiece (3) in such a manner that the link actuator (4) rotates on rotation of the mouthpiece enabling the piercing pins (7) move laterally.

In another embodiment of the present invention, a link actuator may be replaced or substituted by a link member or a horse-shoe shape member, or any suitable alternate embodiment which serves to move the piercing pin(s) on opening/closing of the mouthpiece.

Another embodiment of the present invention provides a method for piercing a capsule or similar suitable medicament receptacle in an inhaler device according to the present invention.

In the following description the terms housing and lower body are used interchangeably.

In one aspect, the present invention provides an inhalation device comprising a lower body (1) having a medicament or capsule holder (2) to hold the capsule or similar suitable medicament receptacle; a mouthpiece (3) laterally pivoted to the lower body (1) to rotate about an axis; a link actuator (4) adapted to rotate on rotation of the mouthpiece (3) and being held in the lower body (1); one or more piercing pins (7) for piercing capsules or similar suitable medicament receptacle and being adapted to a link (5); characterized in that the mouthpiece rotates the link actuator (4) that moves the piercing pin(s) linearly to pierce the capsule or similar suitable medicament receptacle in a partial open/closed position of the mouthpiece; and wherein the device comprises an air inlet and an air outlet defining an inhalation passage therebetween, the passage comprising one or more vents.

An inhalation device according to the present invention (as shown for example in FIGS. 1, 2, and 3) generally comprises a lower body (1) having a capsule holder (2) for holding capsules or similar suitable medicament receptacle, (10); said capsule holder (2) having an air inlet (11) and an outlet (12); a mouthpiece (3) pivoted laterally to the lower body (1) so as to rotate about an axis and thereby open and close the outlet (12) of the capsule holder (2). The capsule holder (2) is preferably adapted to receive one or more piercing pins (7) that are held in retracted position in a piercing pin holder (6). The piercing pins (7) are operated by a link (5) that enables the linear movement of the piercing pin (7) to pierce the capsule or similar suitable medicament receptacle (10) and retract back.

According to another embodiment of the present invention, the mouthpiece (3) is opened to place the capsule or similar suitable medicament receptacle (10) in the capsule holder (2). On opening the mouthpiece (3) to full open position as shown in FIG. 1, the link actuator (4) rotates the link (5) thereby the piercing pins (7) are retracted. On closing the mouthpiece (3) for inhalation, in a partially open/closed position, the piercing pin(s) (7) pierces the capsule or similar suitable medicament receptacle (10) in the capsule holder (2) as shown in FIG. 2. On fully closing the mouthpiece (3), the link actuator (4) rotates and retracts the piercing pin from the medicament holder (2).

According to another embodiment of the present invention, a cover member (8) (for example illustrated in FIGS. 1-3 and FIG. 19) may be attached to the housing or may be moveable relative to the housing. The cover member may be rotatable relative to the housing. For example, it may pivot about the same point as the closure means and housing pivot with respect to each other. The cover member preferably comprises locking means enabling it to lock with the housing. The cover member serves to cover the piercing pin holder, pins, and the link/link actuating mechanism. Preferably the cover member comprises means for locking with the holder when the device is in the assembled state.

In another aspect of the invention, there is provided a holder for a medicament, suitably a dry powder medicament capsule, which holder comprises a chamber suitable for receiving a medicament capsule; and means for generating turbulence in a fluid flow through the chamber such that, in use, the turbulent fluid flow causes vibration of a capsule received by the chamber so as to assist in releasing medicament contained within the capsule.

The present medicament holder maximizes the turbulence in the chamber thereby enhancing drug dispersion and delivery.

The means for generating turbulence preferably also holds, or partially holds, a medicament capsule within the holder. Preferably, the means for generating turbulence holds one end of a medicament capsule. Preferably the capsule is held loosely (either completely, partially or at one end). Suitably, this means that any significant movement of the capsule is prevented but the capsule is still enabled to make small vibratory movements within the chamber. The means for generating turbulence may be any suitable means but preferably comprises one or more projections or flow barriers extending from the inner walls of the chamber. The or each projection may, for example, comprise a flat or polygonal facet, or one or more grooves, ridges, helices, rings, or spheres. The means may, for example, comprise one or more transverse, or substantially transverse, projections (relative to the longitudinal axis of the chamber). By polygonal we mean that the projection or barrier presents several faces to the inside of the chamber. For example, in cross section, the means for generating turbulence may be substantially triangular or square, or pentagonal, or hexagonal and so on.

The holder is preferably such that the diameter of the space defined by the means for generating turbulence relative to the diameter of a medicament capsule placed in the holder is such that the capsule is held loosely by the means for generating turbulence. The chamber may be any suitable shape, for example cylindrical or conical. Preferably, it is substantially conical.

Preferably the length of the chamber is optimised. Chamber lengths of between about 15 to 30 mm may for example be used. We have found particularly good performance with a chamber length of 22 mm+/−10%.

Preferably, the means for generating turbulence (or flow barrier) is or are of increased height compared to the means (16) illustrated in FIG. 11 of WO 2006/051300, relative to the axial length of the medicament chamber (14). Preferably, the means for generating turbulence extends substantially the entire length of the medicament chamber—that is, substantially from top to bottom. We have found that increasing the height of the turbulence—generating means in this way results in reduced retention of medicament in the chamber, and also reduced leakage of medicament from around the top of the chamber. Thus, in a preferred embodiment the projections (16) illustrated in FIG. 11 of the present application extend to substantially the top of medicament chamber (14), preferably so that they align with the upper rim of the chamber (14). This is illustrated in FIG. 26 which shows projections (16) extending to the top of the chamber (14).

The holder suitably comprises one or more openings in the sidewalls of the chamber. Preferably, one or more of the openings is provided with guide means for receiving the piercing means, for example one or more piercing pin. Preferably, the guide means protrudes to the exterior of the holder.

The holder preferably comprises a chamber provided with an air inlet and an air outlet. Preferably, the air inlet and air outlet are arranged at opposing ends of the chamber.

The holder may comprise a mesh, and suitably the mesh is provided in the vicinity of the air outlet, the mesh preventing the medicament capsule contained within the chamber to be moved through the air outlet by inhalation during use of the holder. The mesh may be provided as an integral or non-integral component of the holder. For example, the mesh may be manufactured as a separate part and attached to the lower body by a hinge at the pivot point between the mouthpiece and lower body. Alternatively, or in addition, the mesh may be provided within the mouthpiece as described above.

The invention also provides an inhaler device comprising a holder according to the invention, as described herein.

The inhaler device and medicament holder according to the present invention can be manufactured by standard methods well known in the art, as will be apparent to the skilled reader.

The capsule holder (2) according to the present invention, an embodiment of which is shown in FIGS. 11 to 17, is preferably substantially conically shaped and preferably comprises an air inlet (11) at one end and an air outlet (12) at the opposition end. The diameter of the air inlet (11) is preferably substantially less than, and the air outlet (12) preferably larger than the capsule diameter. The capsule holder (2) encloses a medicament cavity or chamber (14) for retaining medicament or a capsule containing medicament. The inner wall (12a) of the capsule holder (2) comprises means for generating turbulence (16) in a fluid flow through the chamber. The means for generating turbulence (16) according to the present invention restricts the free flow of air through the chamber (14) thereby causing maximum turbulence in the chamber (14). This turbulence enhances the vibration of the medicament or capsule containing the medicament in the chamber (14) thereby increasing the drug delivery. The means for generating turbulence (16) enables maximum turbulence to be produced with less volume of air during inhalation thereby enabling the user to inhale a substantially full dose of medicament with less effort. Preferably, the means for generating turbulence (16) holds or partially holds the, or part of the, capsule containing the medicament.

According to one embodiment of the present invention, the internal geometry of the capsule holder is different from the outer shape of the capsule holder. Preferably, the capsule holder has a smooth outer wall.

According to another embodiment of the present invention, the means for generating turbulence (16) is a projection (16) as shown in FIG. 11. For example, four projections as can be appreciated from FIG. 12 may be provided on the inner wall (12a) of the capsule holder (2) that traverse along the holder from the bottom of the holder to above the center of the holder. The number and shape of the projections used can vary widely, but should be such as to produce turbulence within the holder.

In a preferred aspect of the present invention, the facet of the or each projection (16) is flat. Other facet shapes may be used, including polygonal projections. The shape of the projections may also includes grooves, helices, slanting, ridges, spheres, rings and the like so as to provide turbulence in air flowing through the holder.

The capsule holder (2) according to the present invention may be used in inhaler devices with or without a piercing mechanism. According to an embodiment of the invention, the holder is provided with one or more openings (18) on the sidewalls to enable the piercing means that pierce the capsules to pass through the chamber.

To illustrate the invention, a preferred embodiment thereof will now be described with reference to the accompanying drawings (which in no way restrict the scope of the invention and are for the purpose of illustration only) in which:

FIG. 1 is a cross-sectional view of the inhalation device, with piercing means in a fully retracted position and the inhaler mouthpiece in a fully opened position.

FIG. 2 is a cross-sectional view of the inhalation device, with piercing means in a fully extended piercing position and the inhaler mouthpiece in a partially open/partially closed position, and illustrates a preferred position of the vents.

FIG. 3 is a cross-sectional view of the inhalation device, with piercing means in a fully retracted position and the inhaler mouthpiece in a fully closed position.

FIG. 18 shows a perspective view of a mouthpiece.

FIG. 19 shows a perspective view of a cover member.

FIG. 20 shows a perspective view of a housing.

FIG. 21 shows a perspective view of a linking means.

FIG. 22 shows a perspective view of a link actuator.

FIG. 23 shows a perspective view of a pin holder.

FIG. 24 shows a perspective view of a pin.

Figure 4:
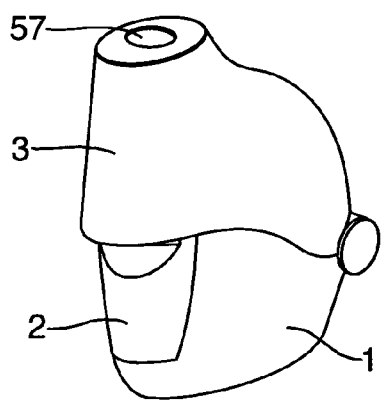
FIG. 4 is a perspective view of the exterior of the inhalation device with the mouthpiece in the fully closed position.
Figure 5:
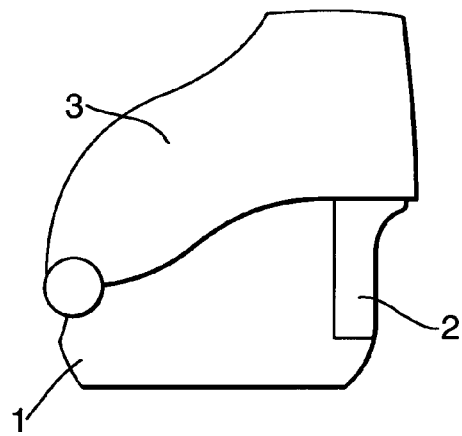
FIG. 5 is a plan view of a side of the inhalation device with the mouthpiece in the fully closed position.
Figure 6:
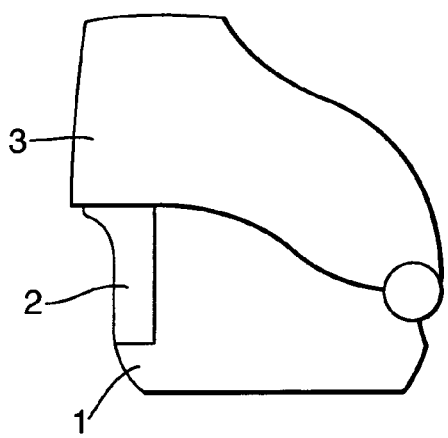
FIG. 6 is a plan view of the other side (with respect to FIG. 5) of the inhalation device with the mouthpiece in the fully closed position.
Figure 7:
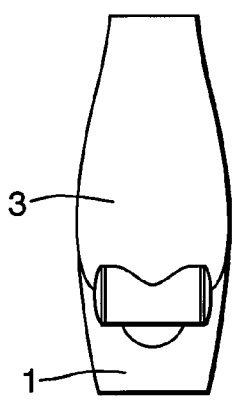
FIG. 7 is a plan view of the rear of the inhalation device with the mouthpiece in the fully closed position.
Figure 8:
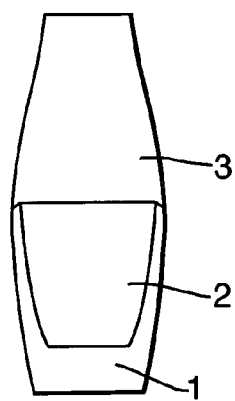
FIG. 8 is a plan view of the front of the inhalation device with the mouthpiece in the fully closed position.
Figure 9:
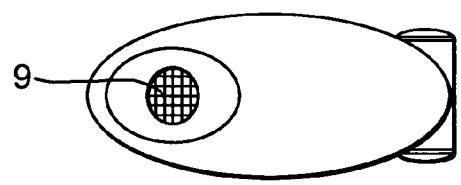
FIG. 9 is a top end view of the inhalation device with the mouthpiece in the fully closed position, viewed from the mouthpiece end.
Figure 10:
FIG. 10 is a bottom end view of the inhalation device with the mouthpiece in the fully closed position, viewed from the lower body end.

A preferred embodiment of the inhalation device is shown in FIGS. 1 to 10 of the accompanying drawings. A preferred embodiment of the capsule holder is shown in FIGS. 11 to 17.

The inhalation device comprises a lower body (1) and a mouthpiece (3) attached to the lower body by a pivot (30) about which the mouthpiece (3) is rotatable. The pivot also serves to secure the mouthpiece (3), lower body (1), link actuator (4) and body cover (8) together. The lower body comprises a capsule holder (2) comprising a chamber (14) adapted to receive a medicament-containing capsule, such as a dry powder medicament containing capsule. In use, a capsule is placed into the chamber (14).

The inhalation device comprises piercing pins (7), located within the lower body (1) and connected to the mouthpiece (3) via a link (5) and link actuator (4). The piercing pins (7) are moveable between a retracted position, shown in FIGS. 1 and 3, and an extended piercing position, shown in FIG. 2. In the fully extended position, the piercing pins (7) are extended into the chamber (14) of the capsule holder (2) through openings (18) in a side wall of the capsule holder (2). In the fully extended position, the piercing pins will pierce a capsule (10) positioned within the chamber (14).

In one embodiment, guide means (20) extend from the openings (18) in a side wall of the chamber. The guide means (20) are positioned so as to guide the movement of the piercing pins (7) between fully extended and fully retracted positions. The guide means (20) can be best appreciated from FIGS. 11 to 17.

Referring to particularly FIGS. 1 to 3, during use of the inhaler, the mouthpiece (3) is rotated to a fully open position in order to insert a capsule into the housing, and then rotated to the closed position to close the housing and position the mouthpiece correctly for inhalation of medicament from the inhaler device. Rotation of the mouthpiece (3) causes rotation of the linking actuator (4), which rotation in turn drives movement of an assembly comprising link (5), piercing pin holder (6) and piercing pins (7). When the mouthpiece (3) is in either the substantially fully closed or substantially fully open position the piercing pins (7) are in a fully retracted, non-piercing position; when the mouthpiece (3) is partially open/partially closed, preferably in a position midway between fully closed and fully open positions, the piercing pins (7) are in a fully extended piercing position. Movement of the mouthpiece (3) from a fully open to a fully closed position causes movement of the piercing pins (7) from a fully retracted position (when the mouthpiece (3) is in the fully open position) to a fully extended piercing position (when the mouthpiece (3) is in a position substantially midway between fully closed and fully open) and returns the piercing pins (7) to a fully retracted position when the mouthpiece (3) is in the fully closed position. Similarly, movement of the mouthpiece (3) from a substantially fully closed to a substantially fully open position causes movement of the piercing pins (7) from a fully retracted position to a fully extended piercing position (when the mouthpiece (3) is in a partially open/partially closed position) and returns the piercing means (7) from a fully extended piercing position to a fully retracted position. Although in a preferred embodiment the pins are fully extended when the mouthpiece (3) is about midway between open and closed, it will be understood that the fully extended position of the pins may be achieved when the mouthpiece (3) (or the closure means) is at any position between the open and closed positions, depending on the precise design of the device.

A mesh (9) is positioned in the mouthpiece (3) so as to align with the outlet (12) of the capsule holder (2) when the mouthpiece (3) is in the fully closed position. When the mouthpiece (3) is closed and the mesh (9) is positioned over the outlet (12), the mesh (9) retains a capsule (10) received in the chamber (14) of the capsule holder (2), preventing the capsule (10) from falling out of the inhaler, or being sucked into the outlet/mouthpiece on inhalation by the user. The mesh size can be any suitable size but is preferably of the order of 0.5 mm×0.5 mm square to 2 mm×2 mm square. More preferably, the mesh size is 1 mm×1 mm square+/−10%. The capsule holder (2) is also provided with locking means. The locking means may be used to lock the mouthpiece (3) in a predetermined position relative to the housing, for example in the fully closed position, and may be located at any suitable place on the device The locking means may comprise a lip or suitable projection (32) adapted to be received by a portion (34) of the mouthpiece (3), which together cooperate so as to provide a snap-fit when the mouthpiece (3) is closed. The mouthpiece (3) can thus be secured in the fully closed position.

Figure 25:
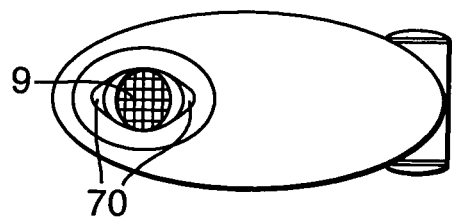
FIG. 25 is a top end view of a preferred inhalation device with the mouthpiece in the fully closed position, viewed from the mouthpiece end. It illustrates the position of the vents.
Figure 26:
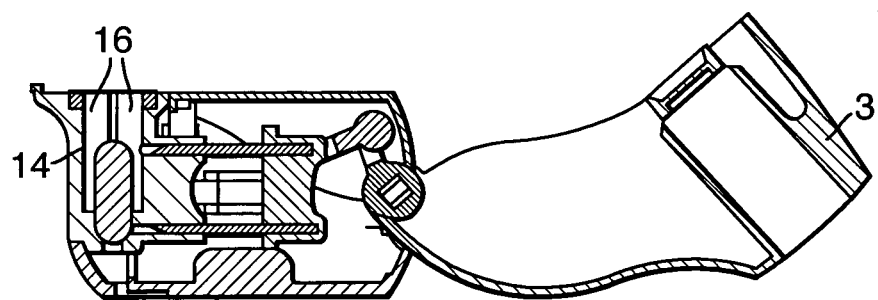
FIG. 26 is a cross-section of a preferred inhalation device illustrating projections (16) of increased height compared to FIG. 11.
Figure 27:
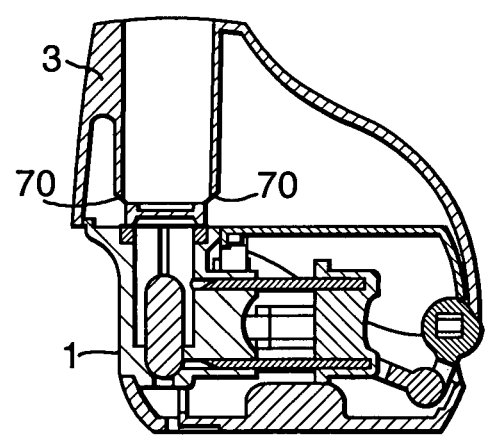
FIG. 27 is a cross-section of a preferred inhalation device and shows a preferred position of the vents.

FIG. 2 illustrates the preferred position of the vents, denoted by the number 70 (the vents themselves are not shown in the drawing). Two crescent-shaped vents are positioned opposing each other on either side of the mesh (9). FIG. 2 also illustrates the primary air inlet (71) on the base of the lower body or housing (1), and the final air outlet (72) on mouthpiece (3). When the device is in the closed position (as in FIG. 3), the device defines an inhalation passage extending through the device between inlet (71) and outlet (72). Vents may be placed at any position in the inhalation passage, although it is preferred to position them upstream of medicament capsule (10); most preferably they are positioned as shown in FIG. 2. FIG. 25 illustrates a preferred position of the vents (70) relative to mesh (9). The exact positioning can be appreciated with reference to FIG. 27 which shows the position of vents (70) relative to the mouthpiece (3) and lower body (1).

A preferred embodiment of the capsule holder (2) is shown in FIGS. 11 to 17. The capsule holder (2) comprises a chamber (14) to receive a capsule and has an air inlet (11) and air outlet (12). Preferably, the chamber (14) is cylindrical or substantially conical and the air inlet (11) and air outlet (12) are located at opposing ends of the chamber (14). A wall of the chamber (14) is provided with openings (18). When the capsule holder (2) is used in combination with the inhalation device of the invention, these openings are positioned so as to receive the piercing pins (7). Guide means (20) extend from the openings (18) to the exterior of the chamber (14), so as to guide the back and forth movement of the piercing pins (7) into and out of the chamber (14) in response to rotation of the mouthpiece (3).

The holder (2) comprises turbulence generating means, for example projections (16), on the interior wall (12a) of the chamber (14). The projections (16) have a dual function: they both hold a capsule (10) received within the chamber (14), and generate turbulence in fluid flow through the chamber (14) and around a capsule (10) received therein.

When a capsule (10) is received in the chamber (14), the projections (16) loosely hold the capsule (10) within the chamber (14). During use of the inhaler, as air is inhaled by the user from the chamber (14) through the outlet (12) and mouthpiece (3), the projections (16) generate turbulence in the air flow through the chamber (14). Turbulence in the air flowing around the capsule (10) causes vibration of the capsule (10) within the chamber (14), and this vibration enhances the dispersion of medicament contained within the capsule (10). Accordingly, less forceful inhalation by the user is required to liberate a full dose of medicament from the capsule (10).

The projections (16) may be of various shapes, such as grooves, ridges, helixes, rings or spheres, or any other shape suitable for generating turbulence in a fluid flow.

The capsule holder (2) is provided with holes (28) which enable the holder (2) to be secured via projections (61) of lower body (1) (see FIG. 20) within an inhalation device. Cooperating means (31) may be provided if desired to enable cooperation with the piercing pin holder (6): this may further assist with alignment of the piercing means.

FIGS. 18 to 24 show various components of a preferred embodiment. FIG. 18 shows a closure means or mouthpiece (3) comprising connecting means (40) which enable the mouthpiece to connect to cylindrical portion (58) of link actuator (4) (see FIG. 22). Mouthpiece (3) also comprises opening (57) via which medicament is inhaled by the user. Means to receive air (for example a tube) from an outlet of the housing, extends downwards from opening (57) within the mouthpiece (not shown in the Figure).

FIG. 19 shows a cover member (8) comprising eyes (41) and notch (48). An equivalent notch is provided on the corresponding side of the cover. In use notches (48) insert in corresponding recesses (49) on lower body (1) (see FIG. 20), so as to lock the cover member and housing together. The cover member also comprises a further notch (not shown) on the underside of the left hand edge: in use this inserts in a corresponding recess (29) (see FIG. 11) so as lock the cover member relative to capsule holder (2). Eyes (41) enable positioning of the cover around a (preferably two-piece) pivot (30) (refer to FIG. 3) which passes through eyes (41), eyes (42) of the lower body (1) (see FIG. 20), connecting means (40) of the mouthpiece (3), and opening (45) in link actuator (4) (see FIG. 22) when the device is assembled. In use, the cover (8) is positioned inside mouthpiece (3).

FIG. 20 shows lower body (1) comprising eyes (42) for receiving a pivot (30), and recesses (49) to receive notches (48) in cover (8) as described above. (An equivalent recess (49) (not shown) to that illustrated in FIG. 20, is provided on the corresponding side of the housing (1).) The sides (50) of lower body (1) are suitably adapted to receive capsule holder (2).

FIG. 21 shows link (5) comprising two arms comprising eyes (43) and end portion (44) supporting notches (51) (only one notch is shown) on either side. The eyes (43) cooperate with corresponding notches (55) on pin holder (6) (see FIG. 23) and thus enable movement of the piercing means (7) when the link (5) is driven by link actuator (4). Notches (51) are received by eyes (46) on link actuator (4), and are rotatable relative to the said eyes (46).

FIG. 22 shows link actuator (4) comprising substantially cylindrical body (58) which is extended via arms (47) which terminate in eyes (46). The actuator (4) also comprises square hole (45) which receives a corresponding sized square pivot (not shown). Correspondingly square holes (60) in connecting means (40) of mouthpiece (3) enable the link actuator (4) and mouthpiece (3) to be rigidly connected (that is, not rotate with respect to each other). In this way, movement of the mouthpiece (3) relative to the housing (1) enables movement of piercing means (7) via driving of link (5).

Figure 11:
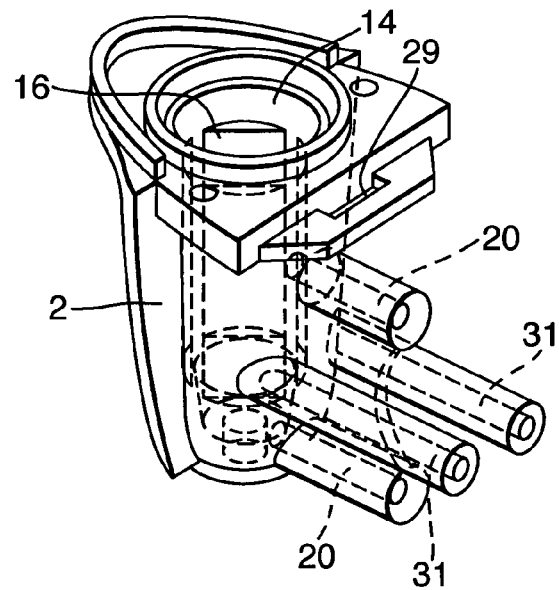
FIG. 11 is a perspective view of a holder for a dry powder medicament capsule.
Figure 12:
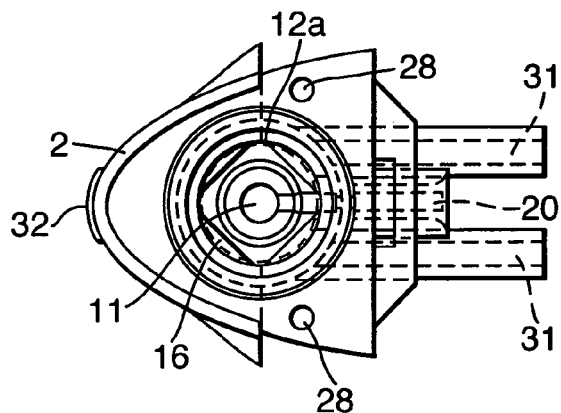
FIG. 12 is an end view of the medicament capsule holder, viewed from the air outlet end.
Figure 13:
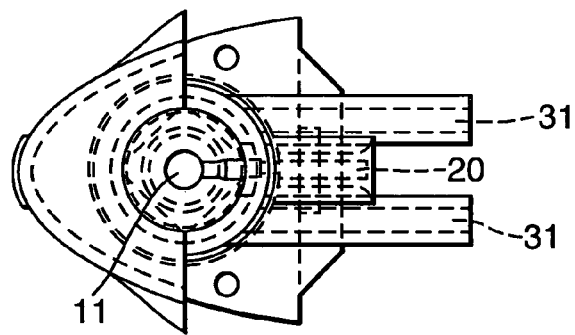
FIG. 13 is an end view of the medicament capsule holder viewed from the air inlet end.
Figure 14:
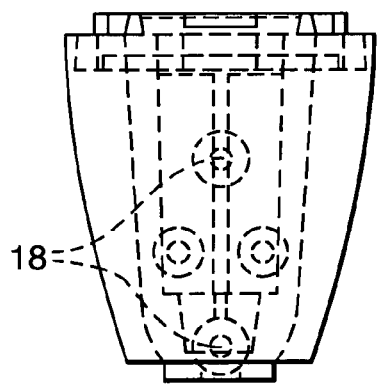
FIG. 14 is a front view of the medicament capsule holder.
Figure 15:
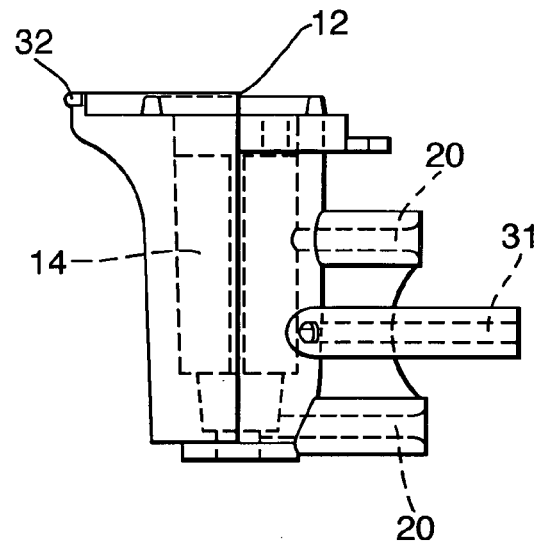
FIG. 15 is a side view of the medicament capsule holder.
Figure 16:
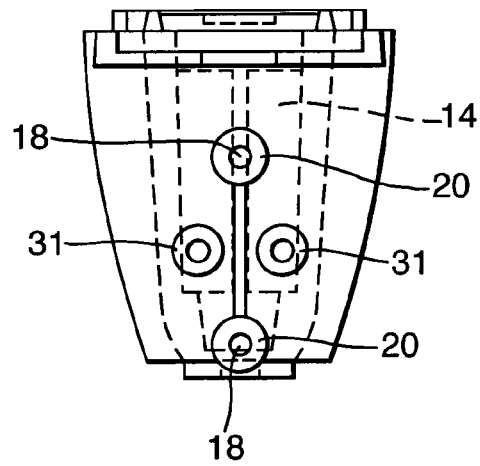
FIG. 16 is a rear view of the medicament capsule holder.
Figure 17:
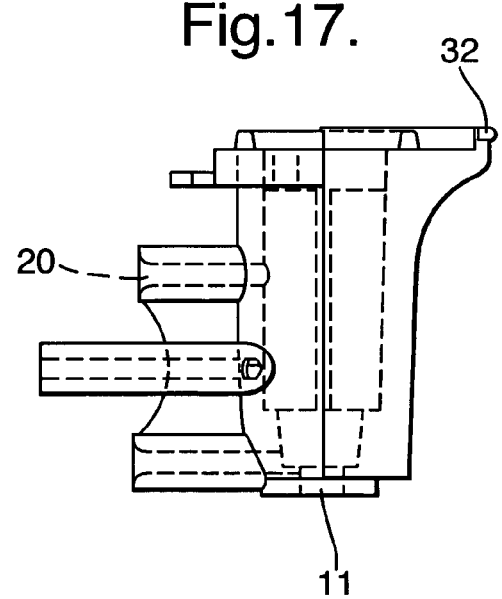
FIG. 17 is a side view of the medicament capsule holder.

FIG. 23 shows piercing pin holder (6) comprising notches (55), as described above, and cylindrical tubes (54) which are adapted to receive attachment means (31) which project from capsule holder (2) (refer to FIG. 11). The cylindrical attachment means (31) are slideable within the tubes (54). In use, pins (7) are mounted in holes (53) (one is obscured in FIG. 23). The pins (not shown in FIG. 23) project beyond tubes (54) and are slideably received within guide means (20) of capsule holder (2).

FIG. 24 shows a preferred piercing means which is a cylindrical pin (7). Preferably, the piercing end of pin (7) comprises a face (56) formed by an oblique cut through the shaft of the pin. Further modification of the piercing end may also be made to achieve the desired shaped point.

The pins may be any suitable size. They may be in a range between 1 mm to 2 mm in diameter, although we prefer to use pins with a diameter of about 1.5 mm+/−10%.

The capsule or medicament holder described is not limited to the embodiments described, and includes various means and forms that may be provided for maximising the turbulence by providing suitable means for generating turbulence in the medicament holder.

The invention claimed is:

1. An inhaler device for inhalation of a medicament from a pierceable capsule, which inhaler comprises:
   a housing for receiving the capsule;
   closure means for closing the housing, said closure means being moveable relative to the housing;
   piercing means suitable for piercing the capsule;
   wherein movement of the closure means relative to the housing causes movement of the piercing means;
   an air inlet and an air outlet defining an inhalation passage therebetween, the inhalation passage comprises one or more vents; and
   a holder for the capsule comprising: a chamber suitable for receiving the capsule; and means for generating turbulence in a fluid flow through the chamber such that, in use, the turbulent fluid flow causes vibration of a capsule received by the chamber so as to assist in releasing medicament contained within the capsule, wherein the means for generating turbulence extends substantially the entire length of the chamber.

2. The inhaler device according to claim 1 wherein the said one or more vents are positioned downstream of the medicament capsule relative to the flow of inhaled air.

3. The inhaler device according to claim 1 wherein movement of the closure means from an open and/or closed position drives movement of the piercing means from a retracted position, and wherein the piercing means moves from a retracted position to an extended piercing position and back to a retracted position in response to movement of said closure means between the open and closed positions.

4. The inhaler device according to claim 1 wherein movement of the closure means moves the piercing means so as to pierce a capsule positioned within the inhaler housing.

5. The inhaler device according to claim 1 further comprising:
   linking means connected to both the closure means and the piercing means; wherein movement of the closure means causes movement of the linking means so as to move the piercing means.

6. The inhaler device according to claim 1 wherein the closure means is rotatable relative to the housing.

7. The inhaler device according to claim 4 wherein movement of the closure means causes rotation of the linking means.

8. The inhaler device according to claim 1 wherein movement of the closure means drives linear displacement of the piercing means.

9. The inhaler device according to claim 1 wherein the closure means is pivotably attached to the housing.

10. The inhaler device according to claim 1 wherein the housing comprises means to hold a medicament capsule, said holding means comprising a chamber having an air inlet and an air outlet.

11. The inhaler device according to claim 10 wherein the air inlet and outlet are provided at opposing ends of the chamber.

12. The inhaler device according to claim 1 wherein the closure means comprises a mouthpiece.

13. The inhaler device according to claim 12 wherein the mouthpiece comprises the one or more said vents.

14. The inhaler device according to claim 11 wherein the mouthpiece comprises means for receiving air from an outlet of the housing, said means being connected to said outlet when the mouthpiece is in its closed position.

15. The inhaler device according to claim 14 wherein the means to receive air from an outlet of the housing comprises the one or more said vents.

16. The inhaler device according to claim 15 wherein the means to receive air from an outlet of the housing comprises a tube.

17. The inhaler device according to claim 12 wherein the means to receive air comprises a mesh which is positioned in proximity to the chamber outlet when the mouthpiece is in a closed position.

18. The inhaler device according to claim 17 wherein the one or more vents are positioned in proximity to the mesh.

19. The inhaler device according to claim 18 wherein two opposing vents are positioned at either side of the mesh.

20. The inhaler device according to claim 1 wherein the device comprises two of said vents.

21. The inhaler device according to claim 1 wherein the or each vent is crescent-shaped.

22. The inhaler device according to claim 14 wherein the length of the means to receive air is from about 25 to 35 mm.

23. The inhaler device according to claim 22 wherein the length of the means to receive air is 31.6 mm+/−10%.

24. The inhaler device according to claim 16 wherein the mesh size is from about 0.5 mm×0.5 mm square to about 2 mm×2 mm square.

25. The inhaler device according to claim 24 wherein the mesh size is about 1 mm×1 mm square+/−10%.

26. The inhaler device according to claim 1 which device further comprises locking means to lock the closure means relative to the housing.

27. The inhaler device according to claim 1 wherein the piercing means comprises one or more piercing pins.

28. The inhaler device according to claim 27 wherein the one or more pins have a diameter of from about 1 mm to about 2 mm.

29. The inhaler device according to claim 28 wherein the one or more pins have a diameter of about 1.5 mm+/−10%.

30. The inhaler device according to claim 1 further comprising guide means to guide the movement of the piercing means.

31. The inhaler device according to claim 1 wherein the means for generating turbulence comprises one or more projections extending from one or more inner walls of the chamber.

32. The inhaler device according to claim 31 wherein the or each projection comprises independently one or more grooves, ridges, helixes, rings, or spheres.

33. The inhaler device according to claim 31 wherein at least one of the one or more projections comprises a flat facet.

34. The inhaler device according to claim 31 wherein each of the one or more projections presents two or more sides or faces to the interior of the chamber.

35. The inhaler device according to claim 1 wherein the means for generating turbulence also holds or partially holds a medicament capsule within the holder.

36. The inhaler device according to claim 35 wherein the means for generating turbulence holds one end of the capsule.

37. The inhaler device according to claim 1 wherein the means for generating turbulence loosely holds a medicament capsule.

38. The inhaler device according to claim 1 wherein the diameter of the space defined by the means for generating turbulence relative to the diameter of a medicament capsule placed in the holder is such that the capsule is held loosely by the means for generating turbulence.

39. The inhaler device according to claim 1 further comprising one or more openings in one or more walls of the chamber.

40. The inhaler device according to claim 39 wherein one or more of the openings is provided with guide means for receiving piercing means.

41. The inhaler device according to claim 1 wherein the chamber is provided with an air inlet and an air outlet.

42. The inhaler device according to claim 41 wherein the air inlet and air outlet are arranged at opposing ends of the chamber.

43. The inhaler device according to claim 41 wherein a mesh is provided in the vicinity of the air outlet, said mesh preventing a medicament capsule within the chamber to be moved through the air outlet by inhalation during use of the holder.

44. The inhaler device according to claim 43 wherein the mesh size is from about 0.5 mm×0.5 mm square to 2 mm×2 mm square.

45. The inhaler device according to claim 44 wherein the mesh size is about 1 mm×1 mm square+/−10%.

46. The inhaler device according to claim 1 wherein the chamber comprises one or more steps.

47. The inhaler device according to claim 1 wherein the length of the capsule chamber is from about 15 mm to about 30 mm.

48. The inhaler device according to claim 47 wherein the length of the capsule chamber is 22 mm+/−10%.

\* \* \* \* \*

UNITED STATES PATENT AND TRADEMARK OFFICE
CERTIFICATE OF CORRECTION

PATENT NO.        : 8,522,775 B2
APPLICATION NO.   : 12/305199
DATED             : September 3, 2013
INVENTOR(S)       : Malhotra et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1121 days.

Signed and Sealed this

Fifteenth Day of September, 2015

Michelle K. Lee
*Director of the United States Patent and Trademark Office*